(12) United States Patent
Paul et al.

(10) Patent No.: US 6,290,909 B1
(45) Date of Patent: Sep. 18, 2001

(54) SAMPLE INJECTOR FOR HIGH PRESSURE LIQUID CHROMATOGRAPHY

(75) Inventors: Phillip H. Paul; Don W. Arnold, both of Livermore; David W. Neyer, Castro Valley, all of CA (US)

(73) Assignee: Sandia Corporation, Livermore, CA (US)

( * ) Notice: Subject to any disclaimer, the term of this patent is extended or adjusted under 35 U.S.C. 154(b) by 0 days.

(21) Appl. No.: 09/548,475

(22) Filed: Apr. 13, 2000

(51) Int. Cl.[7] .................................................... G01N 30/02
(52) U.S. Cl. ........................ 422/70; 73/61.55; 73/61.56; 204/600; 204/647; 210/198.2; 422/100
(58) Field of Search ................................ 422/70, 89, 100; 95/89; 96/105; 436/161; 73/23.41, 61.55, 61.56; 210/198.2, 656, 659; 204/450, 600, 647, 648

(56) References Cited

U.S. PATENT DOCUMENTS 5,922,591 * 7/1999 Anderson et al. .
6,019,882 * 2/2000 Paul et al. .

OTHER PUBLICATIONS

Paul, Phillip H., "Microfluidic Engineering," Sndia Natl. Lab. [Tech. Rep.] Sand (1998), Sand99–8212, pp. 1–21.*
Christensen et al., Anal. Commun. (1998), vol. 35, No. 10, pp. 341–343.*

* cited by examiner

*Primary Examiner*—Jan Ludlow
(74) *Attorney, Agent, or Firm*—Donald A. Nissen

(57) ABSTRACT

Apparatus and method for driving a sample, having a well-defined volume, under pressure into a chromatography column. A conventional high pressure sampling valve is replaced by a sample injector composed of a pair of injector components connected in series to a common junction. The injector components are containers of porous dielectric material constructed so as to provide for electroosmotic flow of a sample into the junction. At an appropriate time, a pressure pulse from a high pressure source, that can be an electrokinetic pump, connected to the common junction, drives a portion of the sample, whose size is determined by the dead volume of the common junction, into the chromatographic column for subsequent separation and analysis. The apparatus can be fabricated on a substrate for microanalytical applications.

11 Claims, 2 Drawing Sheets

SAMPLE INJECTOR FOR HIGH PRESSURE LIQUID CHROMATOGRAPHY

STATEMENT OF GOVERNMENT INTEREST

This invention was made with Government support under contract no. DE-AC04-94AL85000 awarded by the U.S. Department of Energy to Sandia Corporation. The Government has certain rights in the invention.

CROSS-REFERENCE TO RELATED APPLICATIONS

Not applicable.

BACKGROUND OF THE INVENTION

This invention is directed to an apparatus for high pressure injection of a sample into chromatography apparatus generally and into high pressure liquid chromatographic (HPLC) apparatus in particular. The design of this apparatus is such that the phenomenon of sample "tailing" is substantially eliminated. Thus, the apparatus is particularly useful for capillary-based chromatographic systems.

A typical prior art method of injecting a sample into pressure-driven chromatography systems, such as an HPLC apparatus, is illustrated schematically in FIG. 1. Here, a source of pressure, which in conventional chromatography systems is generally a piston or cam-driven pump, is initially, used to force a stream of buffer solution through a packed HPLC column. At the proper time, a sampling valve is turned admitting a portion of a sample into the flowing buffer solution stream and onto the HPLC column where the various components are separated and pass to a detector for analysis. However, for accurate analysis, particularly for complex samples, it is necessary to control precisely the opening and closing of the sampling valve to minimize flow-induced mixing and dead volume, all of which are very difficult to do.

Miniaturization of the chromatography apparatus offers several advantages including, improved efficiency, greater detection sensitivity, low solvent consumption, speed, and the need for only small quantities of sample (typically in the $\mu L$ range). In the extreme, complete microscale chromatography systems have been developed that fit into a single cm-size substrate. Examples of these systems can be found in U.S. Pat. No. 5,885,470 to Parce et al., U.S. Pat. No. 5,858,195 and International Application WO 96/04547 to Ramsey, and U.S. Pat. No. 5,571,410 to Swedberg et al. However, in microanalytical pressure-driven chromatography systems the problem of providing a sample having a well-defined volume is exacerbated. It has been found that it is extremely difficult to define accurately a sample volume injected into the chromatography column since the sample itself is quite small. This is generally a consequence of the fact that sampling valves suitable for pressure-driven microscale chromatography systems are either not available or are incapable of being opened and closed precisely enough to eliminate sample "tailing", flow-induced mixing and dead volume. Moreover, there can be changes in sample composition since faster migrating compounds will be introduced into the chromatography column preferentially. There have been many attempts to alleviate sample "tailing" problem inherent in pressure-driven microanalytical chromatography systems, none have been entirely successful.

SUMMARY OF THE INVENTION

It is an object of this invention to provide an apparatus that provides a clean injection, i.e., sample injection with substantially no tailing, of a sample into pressure-driven chromatography systems.

It is a further object of this invention to provide an apparatus for injecting a sample into an HPLC system that substantially eliminates sample tailing.

It is yet another object of this invention to provide an apparatus for sample injection into a microanalytical HPLC system.

Another object of the invention is to provide a method for sample injection that yields a well-defined sample volume.

A further object is to provide a method for sample injection into microanalytical chromatography systems.

Sample injection into a chromatography system, and particularly into an HPLC system, is accomplished by the present invention by means of electroosmotic/electrophoretic (EO/EP) injection. Here, a conventional sampling valve, such as that illustrated in FIG. 1, is replaced by a pair of injector elements connected in series to a common junction disposed at the inlet to a chromatography column. These elements initiate sample flow through the common junction. At an appropriate time, a pressure pulse from a high pressure pumping system, such as an electrokinetic pump (EKP) drives that portion of the sample residing in the volume of the common junction, and whose size is determined by the volume of the common junction, into the chromatography column. The advantage offered by this means of sample injection is that application of the pressure pulse that drives the sample into the chromatography column eliminates sample leakage from the injector elements thereby providing a well-defined sample plug, i.e., a sample that exhibits substantially no tailing.

DETAILED DESCRIPTION OF THE INVENTION

The present invention is directed to method and apparatus for injecting a sample having a well-defined volume into pressure-driven chromatography systems, and particularly into high pressure liquid chromatography (HPLC) systems. The apparatus provides a substantially "clean" injection, i.e., a sample plug having little or no "tailing" produced by leakage of sample from injector elements subsequent to the step of injection, and thus finds particular application in microanalytical chromatography systems.

Figure 1:
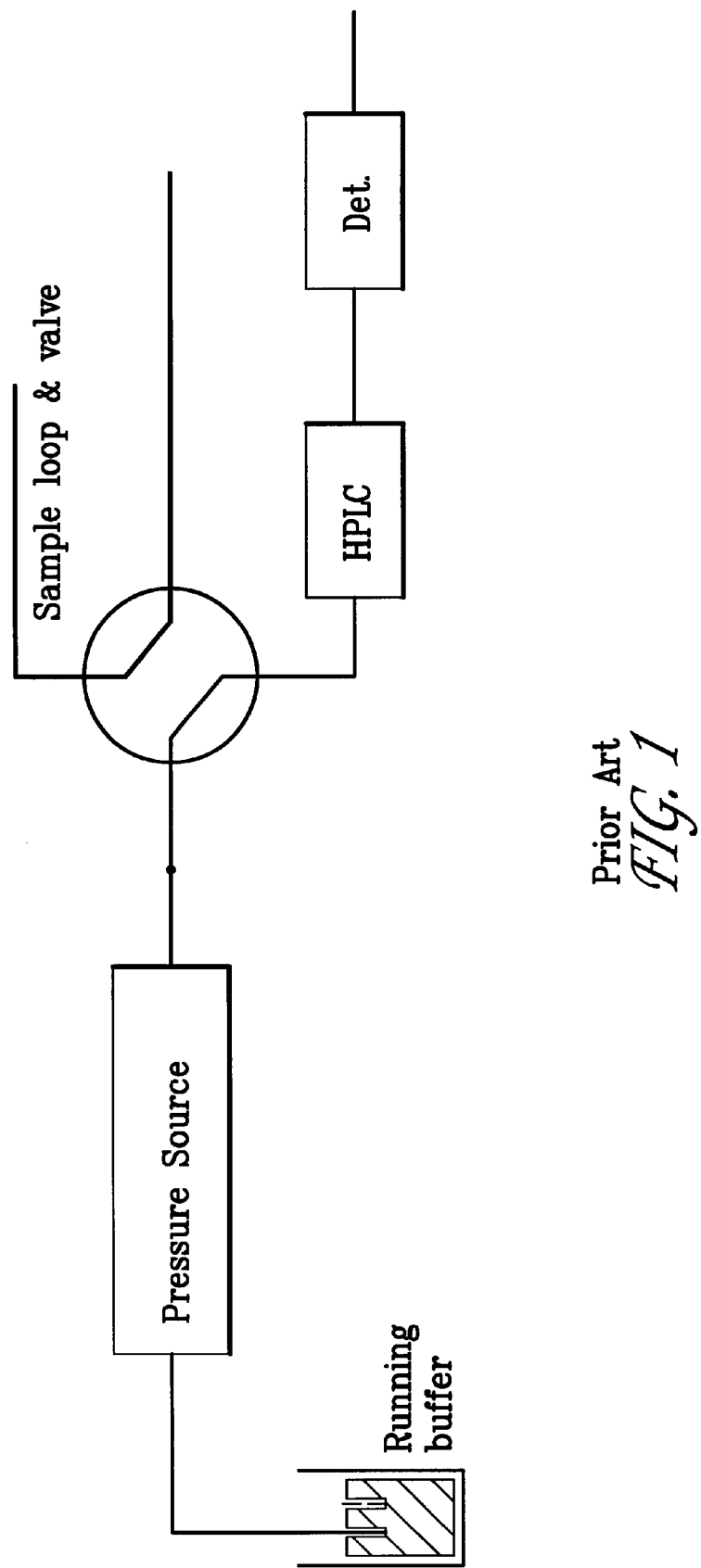
FIG. 1 illustrates a conventional sample injection method.
Figure 2:
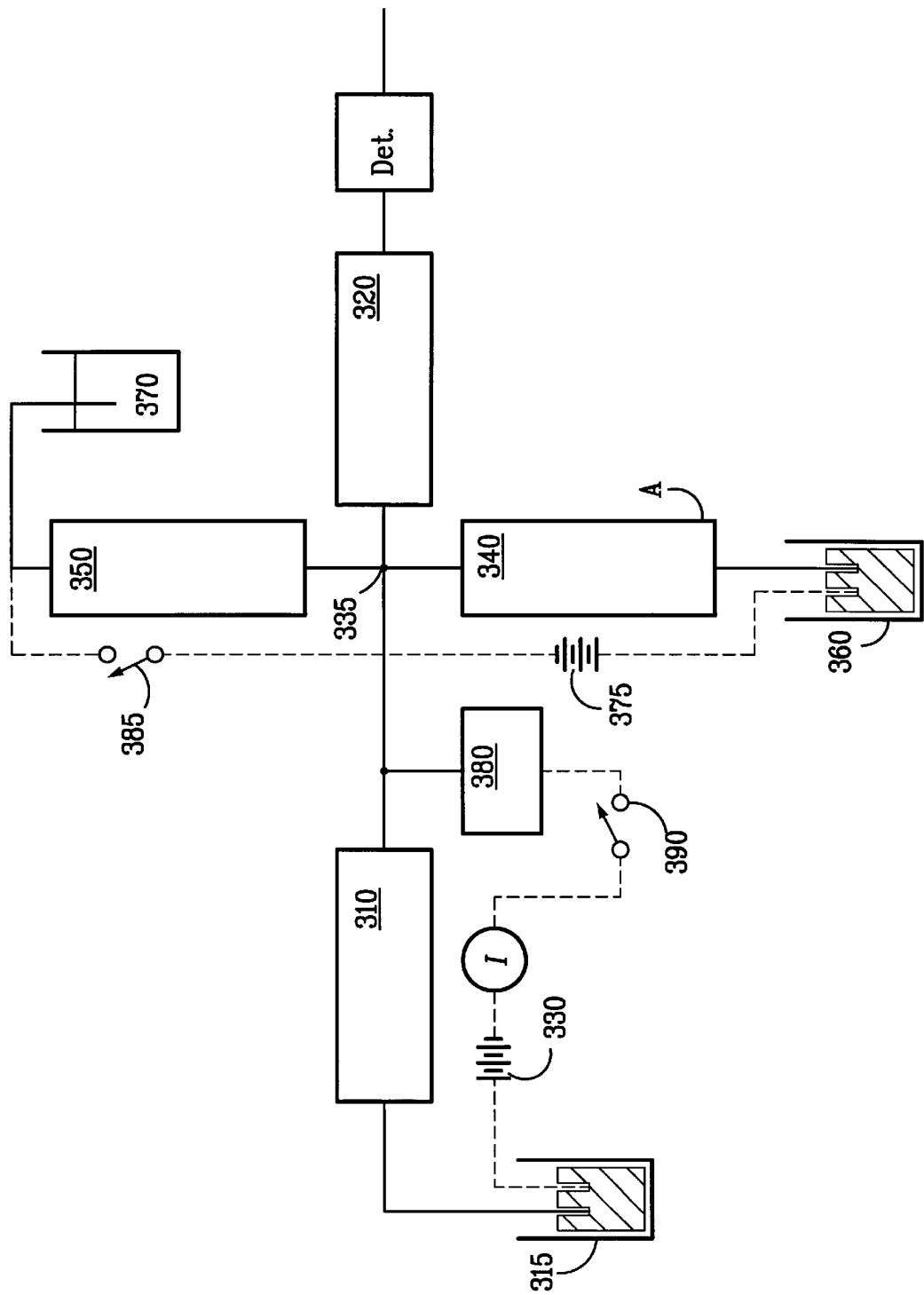
FIG. 2 illustrates an embodiment of the present invention.

The present invention is illustrated and exemplified by the embodiment shown in FIG. 2. Here, a source of hydrostatic pressure 310 is joined at a common junction 335 to an HPLC column 320 to supply a running buffer or other chromatographic fluid 315 to the column. As illustrated in FIG. 2, a preferred hydrostatic pressure source is an electrokinetic pump (EKP). By converting electric potential to hydrodynamic force, an EKP is capable of exerting hydrostatic pressures in excess of 10,000 psi. Moreover, in contrast to prior art pumps, an EKP has no moving mechanical parts and control of pressure and solvent flowrate is achieved simply by controlling the voltage applied to the EKP by voltage source 330. The EKP and its operation has been fully described in U.S. Pat. No. 6,013,164, issued Jan. 11, 2000 and entitled "Electrokinetic High Pressure Hydraulic System" and is incorporated herein in its entirety.

It will be appreciated by those skilled in the art that it is desirable to eliminate the generation of any gases that could arise as a consequence of electrolysis of the EKP electrolyte. This can be accomplished by means known to the art. By way of example, a section of ultra micro-porous material, such as the porous glass sold under the trademark VYCOR, having nominally 4 nm pores, or a membrane such as that sold under the trademark NAFION, saturated with electrolyte can be interposed between the electrode providing connection to the high pressure fluid junction and the junction itself 380. The ultra micro-porous material carries current but the pores are sufficiently fine so that transport of material by pressure-driven or electroosmotic flow is negligible.

A sample injector A is also connected to common junction 335 between hydrostatic pressure source 310 and HPLC column 320. The injector is comprised of at least two elements such as 340 and 350. Each element comprises a container having an inlet and outlet end and filled with a dielectric material to form a porous bed within the container. Containers can include any geometric configuration capable of containing the porous bed of dielectric material, such as capillary tubes, and capable of withstanding pressures of up to about 40,000 psi. Also included are microchannels fabricated on a substrate such as those described by Paul et al. in U.S. Pat. Nos. 6,013,164 and 6,019,882 and by Arnold in prior co-pending U.S. patent application Ser. No. 09/404,945, filed Sep. 9, 1999, now U.S. Pat. No. 6,210,986, entitled "Microfluidic Channel Fabrication Method" assigned to the same assignee. Elements 340 and 350 are connected together in series configuration with a common junction 335. The dielectric material filling each container is selected so as to minimize any chromatographic separation of the sample and can be any non-porous material, known to those skilled in the art, used to form a porous, packed bed. By way of example, the dielectric material can be comprised of uncoated and nonporous silica, glass, or polymer beads or a porous monolithic polymer material. Further, the dielectric material is selected to resist pressure-driven flow but to allow electroosmotically-driven flow. Thus, additionally it is preferred that the pore diameter of the porous bed be in the range of about 25 to 300 nm. One of elements 340/350 serves as a sample inlet and is in communication with a sample container 360 and the other is connected to a waste reservoir 370. A power supply 375 is connected across both elements of sample injector A. Placing one of the electrodes of power supply 375 in the sample container and the other in the waste reservoir can make this connection. Alternatively, power supply 375 can be connected to the elements of the sample injector by means of salt bridges, as discussed above.

One method of injecting a sample into HPLC column 320 can be to run EKP 310 to flush HPLC column 320 with a clean running buffer solution. At an appropriate time, the voltage to EKP 310 is shut off by opening switch 390 and a voltage applied to elements 340 and 350 of sample injector A by closing switch 385, thereby causing liquid to flow from sample container 360 through sample injector A. After a flow of the sample to be analyzed has been established through junction 335, switch 385 is opened to shut off voltage supplied to injector elements 340 and 350. At this point, voltage is once again supplied to EKP 310 thereby causing that portion of the sample that is resident in common junction 335 to be pressure-driven into HPLC column 320 by the running buffer, the volume of the sample being determined by the dead volume of the common junction. As the sample is driven through the HPLC column by the running buffer it is separated into its components, which are detected at the HPLC column outlet.

It should be noted that because the porous bed of dielectric material contained in each of the components of the sample injector has a pore size of about 35 to 300 nm, the bed presents a very high resistance to pressure-driven flow. Thus, these components themselves can act as a form of check valve when, having achieved a high pressure, the electric potential supplied to them is switched off.

The present invention now makes it possible to fabricate a completely pressure-driven microanalytical chromatography system on a substrate. Heretofore, because sampling valves suitable for microscale chromatography systems either were not available or were incapable of being opened and/or closed precisely enough to eliminate sample "tailing", flow-induced mixing and dead volume, pressure-driven microanalytical chromatography systems were precluded. Thus, in a typical microanalytical chromatography systems samples are moved by electroosmotic force, wherein an electric field is applied to cause the sample to move throughout the system in a series of interconnected channels such as those described by Ramsey. However, the use of electroosmotic force to move samples can cause changes in sample composition since faster migrating compounds will be introduced into the chromatography column preferentially. This source of error in microanalytical systems is eliminated by the present invention by the use of pressure-driven sample injection.

It should be noted that in addition to the dielectric materials set forth above that can be placed into a previously fabricated channel disposed on a substrate to comprise the porous bed, other high surface area features such as might be produced by microfabrication methods known to those skilled in the art, preferably by lithographic etching, and which present a porous matrix having a high surface area can be microfabricated directly into the channel.

It will be understood that the described arrangement of apparatus and methods pertaining thereto are merely illustrative of applications of the principles of this and many other embodiments and modifications can be made by those of skill in the art without departing from the spirit and scope of the invention as defined in the claims.

We claim:

1. An apparatus for injecting a sample into a chromatographic column, comprising:
   a source of high pressure joined at a common junction to the inlet of the chromatographic column; and
   a sample injector joined to the common junction, said sample injector comprising at least two elements combined in a series arrangement and connected to a common power supply, wherein each element comprises a container having an inlet end and an outlet end, the container filled with a dielectric material forming a porous bed therein.

2. The apparatus of claim 1, wherein said high pressure source comprises an electrokinetic pump.

3. The apparatus of claim 1, wherein the porous dielectric material is comprised of a nonporous and uncoated material.

4. The apparatus of claim 3, wherein the dielectric material includes a glass, ceramic, or polymer material.

5. The apparatus of claim 4, wherein the dielectric material is silica beads.

6. The apparatus of claim 1, wherein the porous bed has a pore size in the range of about 25 to 300 nm.

7. The apparatus of claim 1, wherein the power supply includes electrodes and further including at least one salt bridge disposed between the electrodes of the power supply and the elements of said sample injector.

8. An apparatus for the high pressure injection of a sample into a chromatography column, comprising:
   a substrate fabricated to define a microchannel system disposed thereon, the microchannel system comprising, in combination,
      a source of high pressure joined at a common junction to the inlet of the chromatography column; and
      a sample injector joined to the to the common junction, said sample injector comprising at least two elements combined in a series arrangement and connected to a common power supply, wherein each element comprises a container having an inlet end and an outlet end, the container filled with a dielectric material forming a porous bed therein.

9. The apparatus of claim 8, wherein the source of high pressure is an electrokinetic pump.

10. The apparatus of claim 8, wherein the power supply includes electrodes and further including at least one salt bridge disposed between the electrodes of the power supply and the elements of said sample injector.

11. The apparatus of claim 8, wherein the dielectric material comprising the porous bed is produced by lithographic etching.

* * * * *